United States Patent
Hwang et al.

(10) Patent No.: US 8,158,411 B2
(45) Date of Patent: Apr. 17, 2012

(54) METHOD OF SEPARATING MICROORGANISM USING NONPLANAR SOLID SUBSTRATE AND DEVICE FOR SEPARATING MICROORGANISM USING THE SAME

(75) Inventors: Kyu-youn Hwang, Yongin-si (KR); Sung-young Jeong, Yongin-si (KR); Joon-ho Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1161 days.

(21) Appl. No.: 11/841,117

(22) Filed: Aug. 20, 2007

(65) Prior Publication Data

US 2008/0044885 A1    Feb. 21, 2008

(30) Foreign Application Priority Data

| Aug. 21, 2006 | (KR) | 10-2006-0079053 |
| Aug. 21, 2006 | (KR) | 10-2006-0079054 |
| Aug. 21, 2006 | (KR) | 10-2006-0079055 |
| Aug. 21, 2006 | (KR) | 10-2006-0079056 |
| Sep. 25, 2006 | (KR) | 10-2006-0092919 |

(51) Int. Cl.
*C12M 1/00* (2006.01)

(52) U.S. Cl. .......... 435/308.1; 435/176; 435/235.1; 435/261

(58) Field of Classification Search .......... 435/176, 435/235.1, 261, 308.1
See application file for complete search history.

(56) References Cited

U.S. PATENT DOCUMENTS

| 3,224,946 | A | * | 12/1965 | Raymond | 435/244 |
| 5,085,779 | A | * | 2/1992 | Crane et al. | 210/635 |
| 5,234,809 | A | | 8/1993 | Boom et al. | |
| 5,260,243 | A | * | 11/1993 | Dunne et al. | 502/68 |
| 5,369,011 | A | * | 11/1994 | Ebersole et al. | 435/7.32 |
| 5,705,628 | A | | 1/1998 | Hawkins | |
| 6,107,053 | A | * | 8/2000 | Contant-Pussard et al. | 435/29 |
| 6,291,166 | B1 | | 9/2001 | Gerdes et al. | |
| 6,337,089 | B1 | * | 1/2002 | Yoshioka et al. | 424/451 |
| 6,498,007 | B1 | | 12/2002 | Adachi et al. | |
| 6,617,105 | B1 | * | 9/2003 | Rudi et al. | 435/6 |
| 6,949,355 | B2 | * | 9/2005 | Yamanishi et al. | 435/34 |
| 2002/0042125 | A1 | | 4/2002 | Petersen et al. | |
| 2006/0234379 | A1 | * | 10/2006 | Lim et al. | 435/378 |
| 2006/0270031 | A1 | | 11/2006 | Hwang et al. | |
| 2007/0264675 | A1 | | 11/2007 | Toner et al. | |
| 2008/0044864 | A1 | | 2/2008 | Jeong et al. | |
| 2008/0044884 | A1 | | 2/2008 | Hwang et al. | |
| 2008/0070282 | A1 | | 3/2008 | Hwang et al. | |

FOREIGN PATENT DOCUMENTS

| EP | 0280647 | A2 | 1/1987 |
| GB | 2152030 | | 7/1985 |
| JP | 63-252252 | A | 10/1988 |
| JP | 02-107182 | A | 4/1990 |
| JP | 02-209814 | A | 8/1990 |
| JP | 1991-232533 | A | 10/1991 |
| JP | 10-506991 | A | 7/1998 |
| JP | 2001-098007 | A | 4/2001 |
| JP | 2002-001329 | A | 1/2002 |
| JP | 2004-267152 | A | 9/2004 |
| JP | 2005-295969 | A | 10/2005 |
| KR | 1019970002624 | B1 | 3/1997 |
| KR | 1020010032806 | | 4/2001 |
| KR | 1020060068979 | | 6/2006 |
| KR | 1020060109254 | A | 10/2006 |
| WO | 9851693 | A1 | 11/1998 |
| WO | 99/09042 | A2 | 2/1999 |
| WO | 9929703 | A2 | 6/1999 |
| WO | 03010278 | A2 | 2/2003 |
| WO | 2004/051231 | A1 | 6/2004 |
| WO | 2004029221 | A2 | 8/2004 |
| WO | 2004087226 | A1 | 10/2004 |
| WO | 2005093065 | A1 | 10/2005 |

OTHER PUBLICATIONS

Cady, NC et al. Nucleic acid purification using microfabricated silicon structures. 2003. 19: 59-66.*
European Search Report dated Mar. 5, 2008 for Application No. 07114674.0-2405.
Lind Bo-Bertil et al., Nutrient recovery from human urine by struvite crystallization with ammonia adsorption on zeolite and wollastonite, Bioresource Technology, Jun. 2000, vol. 73, No. 2, pp. 169-174.
Acarturk et al., Control of attachment, morphology, and proliferation of skeletal myoblasts on silanized glass, Journal of Biomedical materials research, Mar. 15, 1999, vol. 44, No. 4, 355-370.
Liu Q Y et al., Synaptic connectivity in hippocampal neuronal networks cultured on micropatterned surfaces, Developmental Brain Research Apr. 14, 2000, vol. 120, No. 2, Apr. 14, 2000 pp. 223-231.
Spargo BJ, et al., Spatially controlled adhesion, spreading, and differentiation of endothelial cells on self-assembled molecular monolayers, Proceedings of the National Academy of Aciences, USA, vol. 91, Nov. 1994, pp. 11070-11074.
Yang Changming et al., Electrically driven microseparation methods for pesticides and metabolites: III. Capillary electrochromatography with novel silica-based stationary phases having a surface-bound surfactant moiety, Electrophoresis, vol. 21, No. 10, Jun. 2000 pp. 1977-1984.

(Continued)

*Primary Examiner* — Allison Ford
*Assistant Examiner* — Susan E Fernandez
(74) *Attorney, Agent, or Firm* — Cantor Colburn LLP

(57) ABSTRACT

Provided is a method of separating microorganisms from a sample including contacting the sample containing microorganisms with an inorganic ion exchange material such that the sample reacts with the inorganic ion exchange material, and contacting the reacted sample with a means for capturing microorganisms.

9 Claims, 3 Drawing Sheets

OTHER PUBLICATIONS

Absalom, DR et al., "Surface Thermodynamics of Bacterial Adhesion", Applied and Environmental Microbiology, Jul. 1983, pp. 90-97.

Japanese Office Action dated Feb. 1, 2011 issued in JP 2007-214954.

Sia, S.K. et al., Microfluidic devices fabricated in Poly(dimethylsiloxane) for biological studies, Electrophoresis, 2003, 24(21): 3563-3576.

Absolom, D.R. et al., Adhesion of hydrophilic particles (human erythrocytes) to polymer surfaces: Effect of pH and ionic strength, Colloids and Surfaces, vol. 21, 1986, 447-456.

Henriksson, A. et al., Characteristics of the adhesive determinants of *Lactobacillus fermentum* 104, Appl. Environ. Microbiol., 57(2); 1991, 499-502.

Herron, P. R. et al., New Method for Extraction of Streptomycete Spores from Soil and Application to the Study of Lysogeny in Sterile Amended and Nonsterile Soil, Appl. Environ Microbiol. 1990; 56(5): 1406-1412.

Saito, T. et al., Adherence of oral streptococci to an immobilized antimicrobial agent, Arch Oral Biol. Aug. 1997; vol. 42 (8): 539-45.

Ujam, L.B. et al., Cell separation by expanded bed adsorption: use of ion exchange chromatography for the separation of *E. coli* and *S. cerevisiae,* Bioprocess and Biosystems Engineering, vol. 23(3): 245-250, 2000.

Turpin, P.E. et al., An ion-exchange based extraction method for the detection of salmonellas in soil, J. of Applied Bacteriology, 74: 181-190, 1993.

Japanese Office Action issued Aug. 17, 2010 in JP 2007-214954.

Barbe, L., Mecanismes D'Adherence Des Leucocytes Aux Fibres Synthetiques. Application a La Filtration Du Sang, These pour obtenir le grade de docteur a L'Universite Paris 7, U.F.R. de physique, Dec.14, 2001, pp. 1-197. (Eng. abstract).

Wang, Z. et al., Measurements of scattered light on a microchip flow cytometer with integrated polymer based optical elements, Lab Chip, 2004;4: pp. 372-377.

Ikada Y. et al., Surface modification of polymers for medical applications, Biomaterials, 1994;15(10): pp. 725-36.

* cited by examiner

METHOD OF SEPARATING MICROORGANISM USING NONPLANAR SOLID SUBSTRATE AND DEVICE FOR SEPARATING MICROORGANISM USING THE SAME

This application claims the benefit of Korean Patent Application Nos. 10-2006-0079053, 10-2006-0079054, 10-2006-0079055, and 10-2006-0079056, each filed on 21 Aug. 2006, and 10-2006-0092919, filed on Sep. 25, 2006, in the Korean Intellectual Property Office, the disclosure of each of which is incorporated herein in its entirety by reference.

BACKGROUND OF THE INVENTION

1. Field of the Invention

The present invention relates to a method of separating microorganisms from a sample using ion exchange and a means for capturing microorganisms, a container for pretreating a sample containing microorganisms, and a device for separating microorganisms.

2. Description of the Related Art

Methods of separating microorganisms from a sample include centrifugation and filtration. Further, in a method of concentrating and separating particular cells, the cells are allowed to bind specifically to receptors or ligands attached to a surface of a support. For example, an affinity chromatography method includes flowing a sample containing cells over a support to which antibodies capable of specifically binding to the cells are attached, thereby binding the cells to the antibodies and washing out unbound cells.

Further, Korean Laid-Open Patent Publication No. 2006-0068979 describes a cell separation system using an ultrasound field and traveling wave dielectrophoresis. The cell separation system includes a piezoelectric transducer, which is connected to both ends of an upper glass substrate and may convert an electric input from the outside into a mechanical vibration so as to be applied to the upper glass substrate; and electrodes which are arranged on a lower substrate parallel to the upper glass substrate, the number of the electrodes being N. A fluid containing cells can fill the space between the upper glass substrate and the lower substrate. Each of the electrodes is disposed in a vertical direction relative to the longitudinal direction of the piezoelectric transducer and all of the N electrodes are arranged at regular intervals along the longitudinal direction of the piezoelectric transducer.

Thus, in the above methods, specific cells are selectively concentrated or separated from a sample using specific ligands or receptors immobilized on a solid substrate or using an external driving force. However, a method or a device for separating cells by using the properties of a solid support in itself and the conditions of a liquid medium have not been reported yet.

Further, a method of removing materials preventing the cells from binding to the solid support using ion exchange in such a method has not been reported yet.

SUMMARY OF THE INVENTION

The present invention provides a method of separating microorganisms using ion exchange and a means for capturing microorganisms.

The present invention also provides a container for pretreating a sample containing microorganisms in the method of separating microorganisms.

The present invention also provides a device for separating microorganisms using ion exchange and a means for capturing microorganisms.

According to an aspect of the present invention, there is provided a method of separating microorganisms from a sample, the method including: contacting a sample containing microorganisms with an inorganic ion exchange material such that the sample reacts with the inorganic ion exchange material; and contacting the reacted sample with a means for capturing microorganisms such that microorganisms in the sample are captured from the sample.

According to another aspect of the present invention, there is provided a container including an inorganic ion exchange material for pretreating a sample containing microorganisms.

According to another aspect of the present invention, there is provided a device for separating microorganisms from a sample comprising microorganisms, the device comprising: a first container comprising an inorganic ion exchange material for pretreating a sample comprising microorganisms; and a second container comprising a means for capturing microorganisms which is in fluid communication with the first container.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
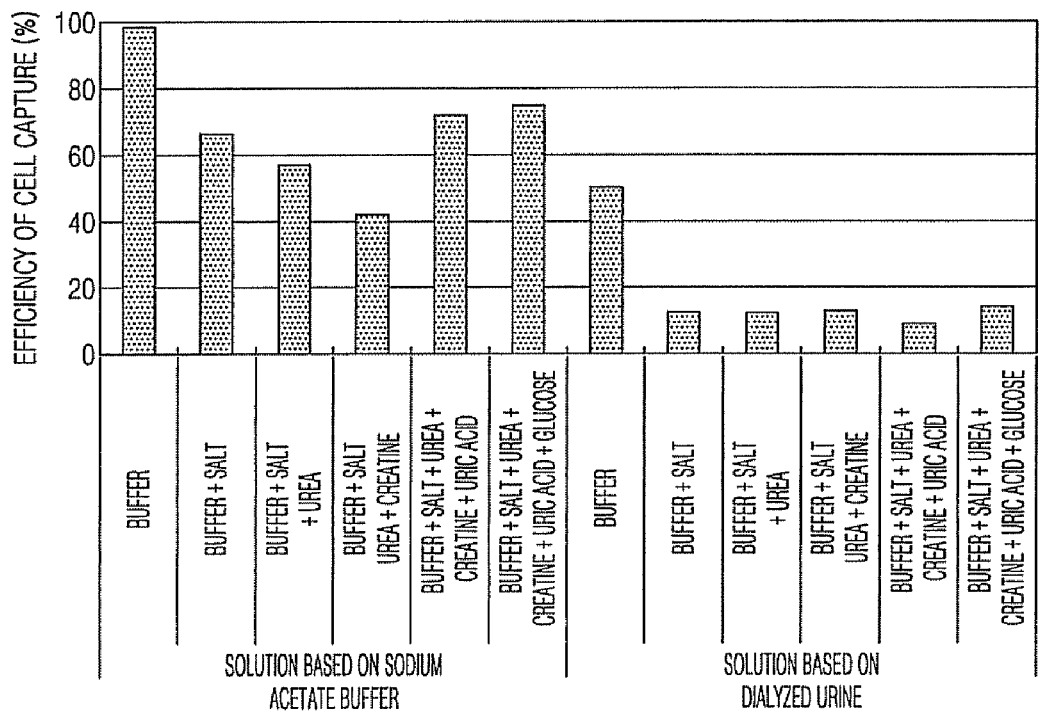
FIG. 1 is a graph illustrating the effect of components of a sample comprising E. coli cells on cell capture efficiencies using a solid support having an array of pillars on its surface, according to an embodiment of the present invention.

Hereinafter, the present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

According to an embodiment of the present invention, there is provided a method of separating microorganisms from a sample, the method including: contacting a sample containing microorganisms with an inorganic ion exchange material such that the sample reacts with the inorganic ion exchange material; and contacting the reacted sample with a means for capturing microorganisms such that microorganisms in the sample are captured from the sample.

The method of separating microorganisms from a sample according to the current embodiment of the present invention includes contacting the sample containing microorganisms with an inorganic ion exchange material such that the sample reacts with the inorganic ion exchange material.

During the contact, ion exchange and adsorption occur between the sample containing microorganisms and the inorganic ion exchange material. Materials which prevent microorganisms from attaching to a solid support such as ionic materials and organic materials may be removed by the ion exchange and adsorption, but the method of removing the materials is not limited thereto.

The sample containing microorganisms can be a biological sample. The term "biological sample" refers to a sample including or consisting of cells or tissues, such as a biological fluid, isolated from an individual. The individual can be an animal such as a human. Examples of the biological sample include saliva, sputum, blood, blood cells (such as leukocytes and erythrocytes), amniotic fluid, serum, semen, bone marrow, a tissue or a microneedle biopsy specimen, urine, a peritoneal fluid, a pleural fluid, and cell cultures. Further, examples of the biological sample include a tissue slice, such as a frozen tissue slice for a histological purpose. In some embodiments, the biological sample is blood, urine, or saliva, specifically urine.

Examples of the microorganisms in the sample can include, but are not limited to, bacteria, fungi, and viruses.

In an embodiment of the present invention, the inorganic ion exchange material can be any inorganic material that has ion exchange properties. Examples of the inorganic ion exchange material can include, but are not limited to, a zeolite, sand, and a metal oxide (e.g, $SiO_2$, $Al_2O_3$, and $Na_2O$). The zeolite can be an H type zeolite.

In the present embodiment, the zeolite is a crystalline aluminosilicate formed by corner-sharing tetrahedral $TO_4$, where T is Al or Si. The zeolite has micropores and channels having a homogeneous molecular size of 1 to 20 Å, and a large surface area of about 900 $m^2/g$. The zeolite is classified into several types such as an H type, a $NH_4$ type, and a Na type zeolite, depending on the presence of a functional group capable of being ionized such as $H^+$, $NH_4^+$, and $Na^+$. The H type zeolite can be obtained by burning the $NH_4$ type zeolite at 550° C. for 2 hours, but the method of obtaining the H type zeolite is not limited thereto. Zeolite Y is commercially available from Aldrich Chemical Co. The zeolite can be a powder or immobilized on the solid support, but the shape of zeolite is not specifically limited.

In contacting the sample with the inorganic ion exchange material according to the current embodiment of the present invention, the sample can be contacted with the inorganic ion exchange material in a solution. The inorganic ion exchange material can be included in a container such as a tube, a microchannel or a microchamber, or immobilized to the inner walls of the bottom of the container. Contacting the sample with the inorganic ion exchange material can be performed at an appropriate temperature (e.g., room temperature) for an appropriate length of time, at least 10 seconds. The experimental conditions can be modified or optimized by those of ordinary skill in the art.

In contacting the sample with the inorganic ion exchange material according to the current embodiment of the present invention, the concentrations of cationic materials such as $Na^+$ and $K^+$ in the sample decrease as a result of an ion exchange reaction between the sample and the inorganic ion exchange material. In this way, salts which prevent microorganisms from attaching to the solid support are removed from the sample. In addition, by contacting the sample with the inorganic ion exchange material, creatine and other materials in the sample that prevent a polymerase chain reaction (PCR) (e.g., urea) are also removed from the sample by adsorption to the ion exchange material.

The method of separating microorganisms from a sample according to the current embodiment of the present invention also includes contacting the reacted sample with a means for capturing microorganisms. The reacted sample indicates the sample having decreased concentration of ionic materials after the ion exchange reaction.

The means for capturing microorganisms can include any material that binds to microorganisms. Examples of the material that binds to microorganisms include, but are not limited to, a solid material, a semi-solid material, and a liquid material. According to an embodiment of the present invention, the means for capturing microorganisms can be a non-planar solid support.

Thus, in an embodiment, the method of separating microorganisms from a sample includes: contacting a sample containing microorganisms with an inorganic ion exchange material such that the sample can react with the inorganic ion exchange material; and contacting the reacted sample with a non-planar solid support in a liquid medium having a pH of 3.0 to 6.0.

The microorganisms can attach to the non-planar solid support by contacting the reacted sample with the non-planar solid support. It is assumed that since the surface area of the non-planar solid support is larger than that of a planar solid support and the use of the liquid medium having a pH of 3.0 to 6.0 denatures cell membranes of the microorganisms resulting in decreased solubility of the cell membranes in the liquid medium, the ratio of the microorganisms that attach to the surface of the non-planar solid support increases under such conditions. However, the scope of the present invention is not limited to this specific mechanism.

In contacting the reacted sample with the non-planar solid support according to the current embodiment of the present invention, the reacted sample may be diluted with a buffer solution capable of buffering the microorganisms at a low pH. The buffer may be a phosphate buffer (such as, sodium phosphate, pH 3.0 to 6.0) or an acetate buffer (such as, sodium acetate, pH 3.0 to 6.0). The sodium phosphate buffer may be 10 mM to 500 mM sodium phosphate buffer, preferably, 50 mM to 300 mM sodium phosphate buffer. The sodium acetate buffer may be 10 mM to 500 mM sodium acetate buffer, preferably, 50 mM to 300 mM sodium acetate buffer. The dilution ratio of the sample with the buffer may be 99:1 to 1:1,000, preferably 99:1 to 1:10, more preferably 99:1 to 1:4, but is not limited thereto.

In contacting the reacted sample with the non-planar solid support according to the current embodiment of the present invention, the reacted sample may have a salt at a concentration of 10 to 500 mM, and preferably 50 to 300 mM. The salts include the salts contained in the buffer solution, such as acetate salts or phosphate salts. The reacted sample may have an ion selected from the group consisting of acetate and phosphate at a concentration of 10 to 500 mM, and preferably 50 to 300 mM.

In contacting the reacted sample with the non-planar solid support according to the current embodiment of the present invention, the non-planar solid support has a larger surface area than a planar solid support. The non-planar solid support can have an uneven structure on its surface. The term "uneven structure" used herein indicates that the surface of the structure is not smooth and has areas that can be concave or convex. The uneven structure can have a surface having a plurality of pillars or a surface having a sieve-like structure with a plurality of pores, but the present invention is not limited thereto.

The non-planar solid support can have any shape and can be a solid support having a plurality of pillars on its surface, a solid support in the form of a bead, or a solid support having a sieve structure with a plurality of pores on its surface. The non-planar solid support can be used alone or in an assembly of a plurality of solid supports (for example, an assembly in a tube or a container).

The non-planar solid support can be a tube, a microchannel of a microfluidic device, or an inner wall of a microchamber. Thus, the method of separating microorganisms from a sample according to the current embodiment of the present invention can be performed in a fluidic device or a microfluidic device having at least one inlet and outlet, wherein the inlet and outlet are in fluid communication with each other through a channel or a microchannel.

As used herein, the term "microfluidic device" incorporates the concept of a microfluidic device that comprises microfluidic elements such as, e.g., microfluidic channels (also called microchannels or microscale channels). As used herein, the term "microfluidic" refers to a device component, e.g., chamber, channel, reservoir, or the like, that includes at least one cross-sectional dimension, such as depth, width, length, diameter, etc. of from about 0.1 micrometer to about 1000 micrometer. Thus, the term "microchamber" and "microchannel" refer to a channel and a chamber that includes at lest one cross-sectional dimension, such as depth, width, and diameter of from about 0.1 micrometer to about 1000 micrometer, respectively.

In an embodiment, the non-planar solid support can be a solid support having a plurality of pillars on its surface. A method of forming pillars on a solid support is well known in the art. For example, a plurality of fine pillars in a high-density structure can be formed on a solid support using photolithography, etc. used in manufacturing semiconductors. The pillars can have an aspect ratio (the height of the pillar:the length of a cross section of the pillar) of 1:1 to 20:1, but the aspect ratio is not limited thereto. The term "aspect ratio" used herein refers to the ratio of the height of the pillar to the length of a cross section of a pillar. When the cross section is a circle, the length of the cross section refers to the diameter of the circle, and when the cross section is a rectangle, the length of the cross section refers to the average length of each side of the rectangle. The ratio of the height of the pillars to the distance between the pillars (height: distance) can be 1:1 to 25:1. The distance between the pillars can be 5 to 100 µm, preferably 5 to 50 µm.

The non-planar solid support can be hydrophobic with a water contact angle of 70 to 95°. The hydrophobicity can be provided by coating a surface of the non-planar solid support with a compound selected from the group consisting of octadecyldimethyl (3-trimethoxysilyl propyl)ammonium (OTC) and tridecafluorotetrahydrooctyltrimethoxysilane (DFS). For example, a $SiO_2$ layer of a non-planar solid support can be coated with a self-assembled monolayer (SAM) of a compound selected from the group consisting of OTC and DFS to provide a water contact angle of 70 to 95°. In this application, the term "water contact angle" refers to water contact angle measured by a Kruss Drop Shape Analysis System type DSA 10 Mk2. A droplet of 1.5 µl deionized water is automatically placed on the sample. The droplet was monitored every 0.2 seconds for a period of 10 seconds by a CCD-camera and analyzed by Drop Shape Analysis software (DSA version 1.7, Kruss). The complete profile of the droplet was fitted by the tangent method to a general conic section equation. The angles were determined both at the right and left side. An average value is calculated for each drop and a total of five drops per sample are measured. The average of the five drops is taken the contact angle.

The non-planar solid support can have at least one amine-based functional group on its surface. The surface of the non-planar solid support having the at least one amine-based functional group can be prepared by coating the surface of the non-planar solid support with polyethyleneiminetrimethoxysilane (PEIM). For example, a $SiO_2$ layer of a non-planar solid support may be coated with a SAM of PEIM. The amine-based functional group is positively charged at a pH of 3.0 to 6.0.

The solid substrate can be a substrate formed of any kind of material that has a water contact angle of 70 to 95° or has at least one amine-based functional group at its surface, or of any kind of material which has a surface which may be coated as described above to obtain a water contact angle of 70 to 95° or to have at least one amine-based functional group at its surface. Examples of the material used to form the non-planar solid support include, but are not limited to, glass, silicon wafer, and plastics, etc.

It is assumed that when the sample containing microorganisms contacts the non-planar solid support having a surface having a water contact angle of 70 to 95° or a surface having at least one amine-based functional group on its surface, the microorganisms attach to the surface of the non-planar solid support. However, the range of the present invention is not limited to this specific mechanism.

The method of separating microorganisms from a sample according to the current embodiment of the present invention may further include washing out substances, other than the target microorganisms, that are not attached to the non-planar solid support after contacting the reacted sample with the non-planar solid support. In the washing, any washing solution that does not separate the attached target microorganisms from the surface of the non-planar solid support but is capable of removing impurities from the sample that can adversely affect subsequent processes may be used. For example, the washing solution can be an acetate buffer or a phosphate buffer used as a binding buffer, etc. That is, the sodium phosphate buffer may be 10 mM to 500 mM sodium phosphate buffer, preferably, 50 mM to 300 mM sodium phosphate buffer. The sodium phosphate buffer may be 10 mM to 500 mM sodium phosphate buffer, preferably, 50 mM to 300 mM sodium phosphate buffer. The washing solution can be a buffer having a pH of 3.0 to 6.0.

The term "separating microorganisms" used herein refers to concentration of the microorganisms or isolation of pure microorganisms.

In the method of separating microorganisms from a sample according to the current embodiment of the present invention, the microorganisms concentrated by attachment to the non-planar solid support can be subjected to a subsequent process, such as isolation of DNA. Alternatively, the microorganisms concentrated by attachment to the non-planar solid support can be eluted from the non-planar solid support and then subjected to a subsequent process, such as isolation of DNA.

Thus, the method of separating microorganisms from a sample according to the current embodiment of the present invention may further include eluting the attached microorganisms from the non-planar solid support after contacting the reacted sample with the non-planar solid support and/or washing. In eluting the microorganisms from the solid support according to the current embodiment of the present invention, the eluting solution may be any known solution that can detach the microorganisms from the non-planar solid support. Examples of the eluting solution include water and Tris buffer, preferably 10 mM to 1000 mM Tris buffer. The eluting solution may have a pH of 6.0 or greater.

According to another embodiment of the present invention, there is provided a method of treating microorganisms. The method of treating microorganisms includes subjecting the microorganisms separated using the method of separating microorganisms from a sample disclosed herein to at least one process selected from: isolation of a nucleic acid, an amplification reaction of a nucleic acid, and a hybridization reaction of a nucleic acid. The isolation of a nucleic acid, the amplification reaction of a nucleic acid, and the hybridization reaction of a nucleic acid can be performed using any methods known in the art.

According to another embodiment of the present invention, there is provided a container including an inorganic ion exchange material for pretreating a sample containing microorganisms.

In the container, the inorganic ion exchange material may be any inorganic material that has ion exchange properties. Examples of the inorganic ion exchange material can include, but are not limited to, a zeolite, sand, and a metal oxide (e.g, $SiO_2$, $Al_2O_3$, and $Na_2O$). The zeolite can be an H type zeolite. Zeolites were described above.

The container can be a tube, a microchannel, or a microchamber. The inorganic ion exchange material can be included in the container or immobilized on the inner walls of the bottom of the container. The container can include an inlet and an outlet through which a sample is injected and discharged. In addition, the container may be a microfluidic device or a lab-on-a-chip including a microchannel and a microchamber.

The container is used for a sample pretreatment process to remove materials from the sample that prevent cells in the sample from attaching to a solid support. The sample pretreatment process comprises contacting a sample containing microorganisms with the inorganic ion exchange material in the container.

According to another embodiment of the present invention, there is provided a device for separating microorganisms from a sample having microorganisms, the device including: a first container including an inorganic ion exchange material for pretreating the sample containing microorganisms; and a second container including a means for capturing microorganisms, which is in fluid communication with the first container.

In the device for separating microorganisms from a sample, the first container including an organic ion exchange material for the pretreatment of the sample containing microorganisms is in fluid communication with the second container including the means for capturing microorganisms.

In the first container, the inorganic ion exchange material may be any inorganic material that has ion exchange properties. Examples of the inorganic ion exchange material were described above.

The inorganic ion exchange material may be included in the first container or immobilized on the inner walls of the bottom of the first container. The first container can be a tube, a microchannel, or a microchamber including the inorganic ion exchange material or to which the inorganic ion exchange material is immobilized. The first container can include an inlet and an outlet through which a sample is injected and discharged. The first container can also be a microfluidic device or a lab-on-a-chip including a microchannel and a microchamber.

The first container is used for a sample pretreatment process to remove materials from a sample that prevent cells in the sample from attaching to the solid support by contacting the sample containing microorganisms with the inorganic ion exchange material in the first container.

In the device for separating microorganisms from a sample according to the current embodiment of the present invention, the second container is in fluid communication with the first container. In addition, the device may further include a valve and a pump in a portion for connecting the first container and the second container, and thus for controlling the amount of the sample moving from the first container to the second container.

The means for capturing microorganisms included in the second container may attach microorganisms to its surface based on properties of the sample containing microorganisms, such as the concentration and pH.

The means for capturing microorganisms may include any material that binds to microorganisms as described above. The means for capturing microorganisms can be a non-planar solid support.

In an embodiment, the device for separating microorganisms from a sample includes: a first container including an inorganic ion exchange material for pretreating a sample containing microorganisms; and a second container including a non-planar solid support, wherein the second container is in fluid communication with the first container.

The non-planar solid support suitable for the second container is as described above. The non-planar solid support has a larger surface area than a planar solid support. The non-planar solid support can have an uneven structure on its surface. The uneven structure may have a surface having a plurality of pillars or a surface having a sieve-like structure with a plurality of pores, but the present invention is not limited thereto.

The non-planar solid support included in the second container can have any shape and can be a solid support having a plurality of pillars on its surface, a solid support in the form of a bead, or a solid support having a sieve structure with a plurality of pores on its surface. The non-planar solid support may be used alone or in an assembly of a plurality of the solid supports (for example, an assembly in a tube or a container).

The non-planar solid support included in the second container may be a tube, a microchannel of a microfluidic device or an inner wall of a microchamber. Thus, the second container can include at least one inlet and outlet and can be a fluidic device or a microfluidic device having at least one inlet and outlet, wherein the inlet and outlet are in fluid communication with each other through a channel or a microchannel. The second container may also be a lab-on-a-chip including the non-planar solid support or to which the non-planar solid support is immobilized. In an embodiment of the present invention, the second container is filled with a non-planar solid support in the form of beads.

The non-planar solid support included in the second container can be a solid support having a plurality of pillars on its surface. The pillars can have an aspect ratio (the height of the pillar:the length of the cross-section of the pillar) of 1:1 to 20:1, but the aspect ratio is not limited thereto. The ratio of the height of the pillars to a distance between the pillars (height:

distance) can be 1:1 to 25:1. The distance between the pillars can be 5 to 100 μm, preferably 5 to 50 μm.

The non-planar solid support included in the second container may have hydrophobicity with a water contact angle of 70 to 95°. The hydrophobicity may be provided as described above.

The non-planar solid support included in the second container can have at least one amine-based functional group on its surface. The support may be coated with PEIM to provide a surface having the at least one amine-based functional group as described above.

The non-planar solid support included in the second container can be formed of any material having a water contact angle of 70 to 95°, any material having at least one amine-based functional group on its surface, or any material which has a surface which may be coated, as described above, to obtain a water contact angle of 70 to 95° or to have at least one amine-based functional group at its surface. Examples of the material used to form the non-planar solid support include, but are not limited to, glass, silicon wafer, and plastics, etc.

Hereinafter, the present invention will be described in more detail with reference to the following examples. However, these examples are for illustrative purposes only and are not intended to limit the scope of the invention.

EXAMPLES

Example 1

Concentrating *E. coli* Cells in a Urine Mimetic Solution Using a Solid Support Having an Array of Pillars on its Surface—Screening Factors Preventing Capture of Cells A sample containing *E. coli* cells was allowed to flow through a fluidic device including a chamber having an inlet and an outlet and having a surface of a silicon chip having an area of 10 mm×23 mm on which an array of pillars was formed, thereby attaching the cells to the surface of the solid support. The number of the bacteria cells in the sample discharged from the fluidic device was determined using colony counting, and then an efficiency of capturing the bacteria cells by the solid support was calculated using the counted number of colonies. In the array of pillars, the distance between the pillars was 12 μm, the height of the pillars was 100 μm, and a cross section of each of the pillars was in the form of a square having sides of 25 μm.

The array of pillars was formed on a $SiO_2$ layer coated with a self-assembled monolayer (SAM) of octadecyldimethyl (3-trimethoxysilyl propyl)ammonium (OTC).

Solutions based on a sodium acetate buffer and solutions based on dialyzed urine, both containing 0.01 $OD_{600}$ of *E. coli* cells, were used as the cell sample.

The solutions based on a sodium acetate buffer (pH 4.0) are as follows:

Buffer: a 100 mM sodium acetate buffer (pH 4.0),

Buffer+salt: a solution having the concentrations of the salts of 88 mM NaCl, 67 mM KCl, 38 mM $NH_4Cl$, and 18 mM $Na_2SO_4$, which was obtained by adding 0.514 g NaCl, 0.5 g KCl, 0.203 g $NH_4Cl$, and 0.259 g $Na_2SO_4$ to a 100 mM sodium acetate buffer (pH 4.0), Buffer+salt+urea: a solution obtained by adding 333 mM urea to the "Buffer+salt" solution, Buffer+salt+urea+creatine: a solution obtained by adding 333 mM urea and 9.8 mM creatine to the "Buffer+salt" solution, Buffer+salt+urea+creatine+uric acid: a solution obtained by adding 333 mM urea, 9.8 mM creatine, and 2.5 mM uric acid to the "Buffer+salt" solution, and Buffer+salt+urea+creatine+uric acid+glucose: a solution obtained by adding 333 mM urea, 9.8 mM creatine, 2.5 mM uric acid, and 0.6 mM glucose to the "Buffer+salt" solution.

The solutions based on dialyzed urine were obtained by mixing dialyzed urine and a 2×-concentrated solution of—each of the solutions above based on the sodium acetate buffer in a ratio of 1:1. The final pH of these solutions was 3.97.

200 μl of each of the samples was allowed to flow from the inlet to the outlet through the chamber at a flow rate of 200 μl/min. The experiments were repeated three times. The number of cells in each of the samples was counted before and after the samples flowed through the chamber having the solid support.

FIG. 1 is a graph illustrating cell capture efficiencies as a function of solution conditions for separating *E. coli* cells from the various tested samples using a solid support having an array of pillars on its surface according to an embodiment of the present invention. Referring to FIG. 1, when salts or other substances were added to the buffer or the buffer:dialyzed urine (1:1) sample, the cell capture efficiencies decreased relative to the cell capture efficiency determined for the buffer or the buffer:dialyzed urine (1:1) sample. Note also that the cell capture efficiency of the buffer:dialyzed urine (1:1) sample was smaller than that for the buffer sample, suggesting that dialyzed urine contains materials that interfere with cell attachment to the solid support.

Example 2

Concentrating *E. coli* Cells in a Urine Solution Using a Solid Support Having an Array of Pillars on its Surface—Determination of Effects of Dilution Ratio of Urine and Flow Rate on Concentrating the Cells A sample containing *E. coli* cells was allowed to flow through a fluidic device including a chamber having an inlet and an outlet and having a surface of a silicon chip having an area of 10 mm×23 mm on which an array of pillars was formed, thereby attaching the cells to the surface of the solid support. The number of the bacteria cells in the sample discharged from the fluidic device was determined using colony counting, and then an efficiency of capturing the bacteria cells by the solid support was calculated using the counted number of colonies. The dimensions of the array of pillars were identical to the array described in Example 1. However, in the current example, the surface of the array of pillars had a SAM coating of PEIM coated on a $SiO_2$ layer.

Samples were prepared as follows. A buffer and urine were mixed in various dilution ratios to obtain a final volume of 1 ml. Then, 10 μl of 1.0 OD *E. coli* cells was added to each of the resulting mixtures.

200 μl of each of the diluted urine samples was allowed to flow from the inlet to the outlet through the chamber at a fixed flow rate (100, 300, or 500 μl/min). The experiments were repeated three times. The number of cells in each of the samples was counted before and after the samples flowed through the chamber having the solid support.

Figure 2:
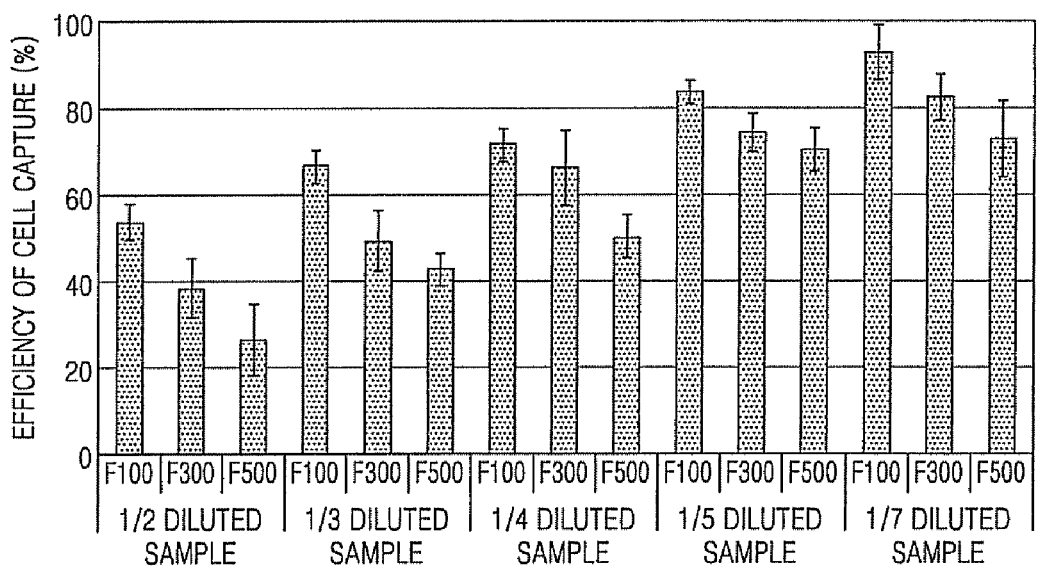
FIG. 2 is a graph illustrating the effect of various dilution ratios and flow rates on cell capture efficiencies from samples comprising E. coli cells, using a solid support having an array of pillars on its surface, according to an embodiment of the present invention.

FIG. 2 is a graph illustrating cell capture efficiencies at various dilution ratios and flow rates for concentrating *E. coli* cells using a solid support having an array of pillars on its surface, according to an embodiment of the present invention. Referring to FIG. 2, at a fixed flow rate, as the dilution ratio of the urine samples increased, the cell capture efficiency increased, and at a fixed dilution ratio, as the flow rate increased, the cell capture efficiency decreased.

As described in Examples 1 and 2, materials preventing microorganisms from attaching to the solid support, such as ionic substances and creatine, are present in the urine samples. Further, when the urine was diluted with a high dilution ratio of generally 5 or greater, the efficiency of capturing the microorganisms by the solid support was high. Therefore, when it is intended to separate the microorganisms from urine using a solid support, these materials should be removed from the urine samples to optimize capture efficiency in the separation process.

Example 3

Effects of Zeolite Treatment on Binding Microorganisms to a Solid Support

Zeolite Y (Aldrich Chemical Co.) ($NH_4$—Y type) was burned at 550° C. for 2 hours to prepare HY (H type zeolite).

30 µl of urine was mixed with 0.3 g of the obtained H type zeolite, and the mixture was mixed with 200 mM of acetate buffer (pH 3.0) (1:1 v/v). Then, *E. coli* cells were added to the mixture to obtain an OD value of 0.01. The control group was prepared in the same manner as above, except that zeolite was not added. Two types of urine were used. The pH of the urine sample (initially having a typical pH ranging from about 5 to about 8) decreased after being mixed with zeolite. For the specific urine samples used in this example, the initial pH values of urine 1: pH 6.2 and urine 2: pH 6.8 were reduced to a pH of 4. The pH of the control group remained unchanged (urine 1: pH 6.2 and urine 2: pH 6.8). Thus, it was assumed that ion exchange occurred in the samples containing the H-type zeolite.

The ion exchanged urine sample was diluted, and contacted with a non-planar solid support to attach microorganisms in the sample to the non-planar solid support. Then, a cell binding efficiency from each of the urine samples was measured.

Ion exchanged urine samples containing *E. coli* cells were allowed to flow through a fluidic device including a chamber having an inlet and an outlet and having a surface of a silicon chip having an area of 10 mm×23 mm on which an array of pillars was formed, thereby attaching the cells to the surface of the solid support. The number of the *E. coli* cells in the sample discharged from the fluidic device was determined by optical density determination, and then an efficiency of capturing the *E. coli* cells by the solid support was calculated using the determined number of the cells. The dimensions of the array of pillars were as described in Example 1. The surface of the array of pillars had a SAM coating of PEIM coated on a $SiO_2$ layer.

Figure 3:
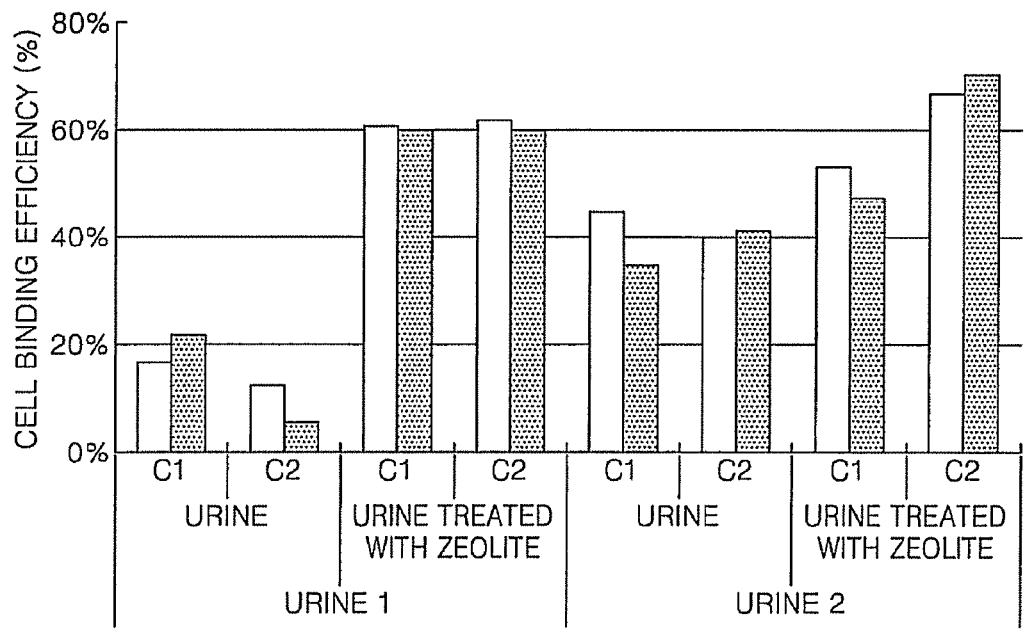
FIG. 3 is a graph illustrating the effect of zeolite treatment of urine samples on efficiency of binding microorganisms to a solid support, according to an embodiment of the present invention.

200 µl of each of the samples was allowed to flow from the inlet to the outlet through the chamber at a flow rate of 200 µl/min. The experiments were repeated two times for each sample. In FIGS. 3-6, C1 and C2 respectively stand for chip 1 and chip 2, for repetition experiments; the black or white bars represent repetition experiments for cell binding efficiency for the same sample type. The cell binding efficiency represents initial cell numbers/unit area—recovered cell numbers/unit area, wherein the initial cell numbers/unit area and recovered cell numbers/unit area represent cell numbers before flowing through the chip and cell numbers after flowing through the chip, respectively. The number of cells were counted by a colony counting method and the black or white bar data were obtained by colony counting after diluting 1/40,000 and 1/80,000 the sample, respectively. FIG. 3 is a graph illustrating the effect of zeolite treatment of urine samples on efficiency of binding microorganisms to the solid support, according to an embodiment of the present invention. Referring to FIG. 3, the samples treated with zeolite had remarkably greater cell binding efficiencies than the samples not treated with zeolite. In particular, for the set of samples labeled "urine 1", the urine samples had low cell binding efficiencies, and the zeolite treatment resulted in a significant increase in the cell binding efficiency observed for each sample. Thus, it is considered that a specific level of cell binding efficiency can be obtained after zeolite treatment, independent of urine.

Example 4

Effects of Zeolite Treatment on Binding Microorganisms to a Solid Support: Effects of NaY Type and $NH_4Y$ Type Zeolite A sodium type zeolite Na—Y and an ammonium type zeolite $NH_4$—Y were obtained from Aldrich Chemical Co.

30 µl of urine was mixed with 0.3 g of either the sodium type zeolite or the ammonium type zeolite. Each zeolite-treated urine was then mixed with 200 mM of acetate buffer (pH 3.0) (1:1 v/v). Then, *E. coli* cells were added to the mixture to obtain an OD value of 0.01. The control group was prepared in the same manner as above except that zeolite was not added. Two types of urine were used. The pH of the urine samples remained unchanged, with the samples based on the two urine types having a pH of 6.2 or 7.0, respectively, after treatment with the NaY type zeolite, and a pH or 5.9 or 6.5, respectively, after treatment with the $NH_4Y$ type zeolite.

The mixture of the urine sample and zeolite was contacted with a non-planar solid support to attach microorganisms in the mixture to the non-planar solid support. Then, a cell binding efficiency from each of the urine samples was measured.

Urine samples containing ion exchanged *E. coli* cells were allowed to flow through a fluidic device including a chamber having an inlet and an outlet and having a surface of a silicon chip having an area of 10 mm×23 mm on which an array of pillars was formed, thereby attaching the cells to the surface of the solid support. The number of the *E. coli* cells in the sample discharged from the fluidic device was determined by optical density determination, and then an efficiency of capturing the *E. coli* cells by the solid support was calculated using the determined number of the cells. The dimensions of the array of pillars were as described in Example 1. The surface of the array of pillars had a SAM coating of PEIM coated on a $SiO_2$ layer.

200 µl of each of the urine samples was allowed to flow from the inlet to the outlet through the chamber at a flow rate of 200 µl/min. The experiments were repeated two times with each type of urine sample.

Figure 4:
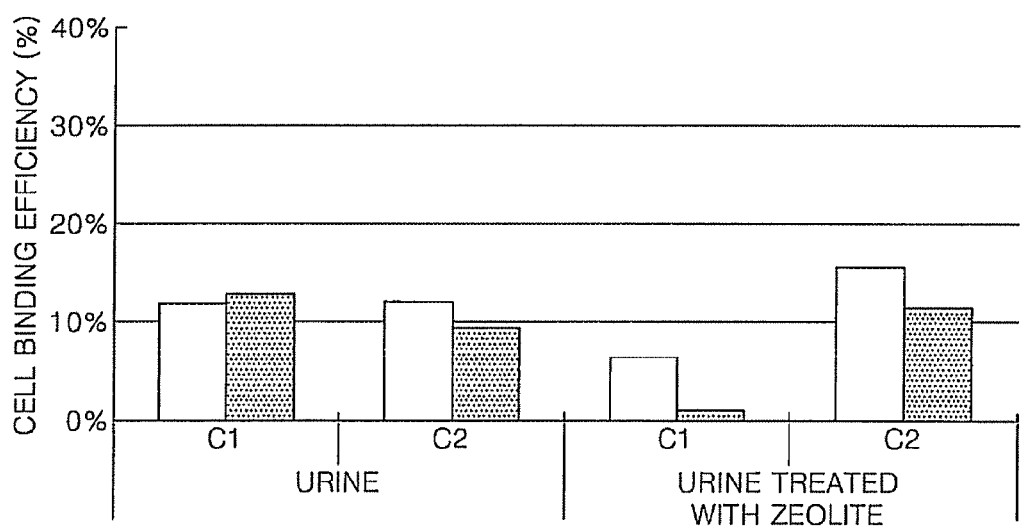
FIG. 4 is a graph illustrating efficiency of binding microorganisms in urine samples mixed with a sodium type zeolite to a solid support, according to an embodiment of the present invention.
Figure 5:
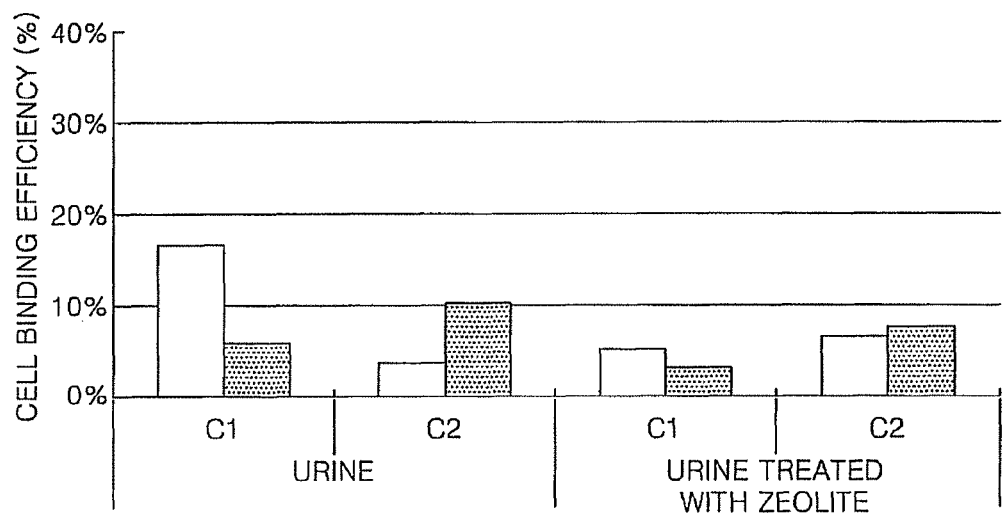
FIG. 5 is a graph illustrating efficiency of binding microorganisms in urine samples mixed with an ammonium type zeolite to a solid support, according to an embodiment of the present invention.

The efficiency of binding microorganisms in the urine samples mixed with the sodium type zeolite or the ammonium type zeolite to a solid support is shown in FIG. 4 or FIG. 5, respectively. Referring to FIGS. 4 and 5, the samples treated with the sodium type zeolite and the ammonium type zeolite had similar or smaller cell binding efficiencies compared to the samples not treated with zeolite. Thus, it is inferred that the pH decrease due to H+ ions obtained from the ion exchange between the H type zeolite and urine sample has an advantageous effect on the cell binding efficiency.

Example 5

Effects of Zeolite Treatment on Binding Microorganisms to a Solid Support: Comparison Between a Diluted Sample and an Undiluted Sample Treated with Zeolite Zeolite Y (Aldrich Chemical Co.) (NH4-Y type) was burned at 550° C. for 2 hours to prepare HY (H type zeolite).

30 µl of urine was mixed with 0.3 g of the obtained H type zeolite (undiluted urine sample). 30 µl of urine was mixed with 200 mM of acetate buffer (pH 3.0) (1:1 v/v) to prepare a control group (two times diluted urine sample). Then, E. coli cells were added to each mixture to obtain an OD value of 0.01. One type of urine sample was used. The pH of the urine sample mixed with the zeolite decreased after mixing with the zeolite from an initial pH of 7.4 to a pH of 3.8. It is assumed that ion exchange occurred. The pH of the control group decreased to pH 4.2 due to the dilution with the buffer.

The ion exchanged urine sample and the control were each contacted with a non-planar solid support to attach microorganisms in the samples to the non-planar solid support. Then, a cell binding efficiency of each of the samples was measured.

Ion exchanged urine samples or the control samples containing E. coli cells were allowed to flow through a fluidic device including a chamber having an inlet and an outlet and having a surface of a silicon chip having an area of 10 mm×23 mm on which an array of pillars was formed, thereby attaching the cells to the surface of the solid support. The number of E. coli cells in the sample discharged from the fluidic device was also determined by optical density determination, and then an efficiency of capturing the E. coli cells by the solid support was calculated using the determined number of the cells. The dimensions of the array of pillars were as described in Example 1. The surface of the array of pillars had a SAM coating of PEIM coated on a $SiO_2$ layer.

200 µl of each of the urine samples was allowed to flow from the inlet to the outlet through the chamber at a flow rate of 200 µl/min. The experiments were repeated two times.

Figure 6:
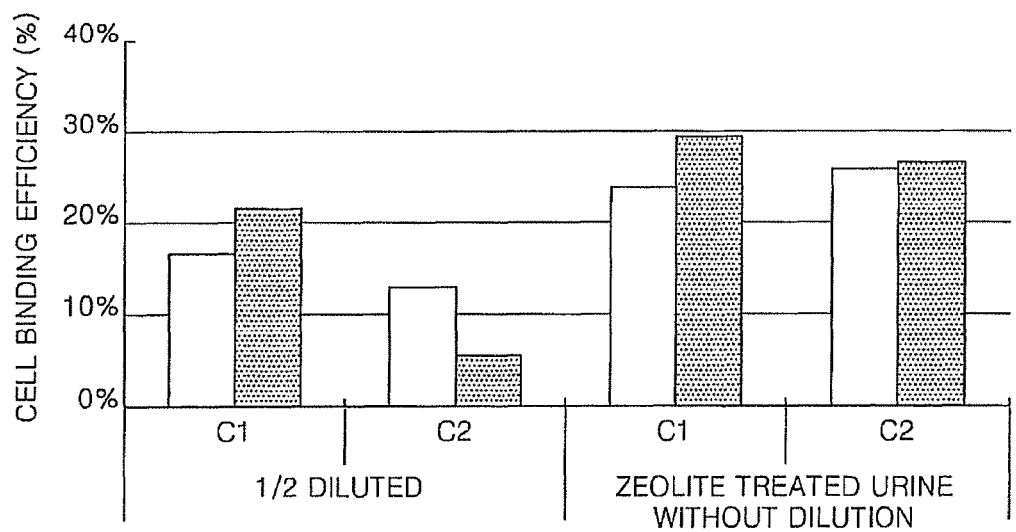
FIG. 6 is a graph illustrating the effect of zeolite treatment of undiluted urine samples on efficiency of binding microorganisms to a solid support, according to an embodiment of the present invention, compared to the efficiency of binding microorganisms from a urine sample diluted 1:1 with a buffer.

FIG. 6 is a graph illustrating the effect of zeolite treatment of urine samples without dilution on efficiency of binding microorganisms to the solid support, according to an embodiment of the present invention. Referring to FIG. 6, the ion exchanged samples without dilution had remarkably greater cell binding efficiencies than the diluted samples. That is, a cell binding efficiency of about 25% of could be obtained after ion exchange without requiring a volume increase in the sample resulting from dilution.

By using the method of separating microorganisms such as bacteria, fungi, or viruses from a biological sample according to the present invention, the microorganisms may be efficiently separated from the biological sample.

By using the container for pretreating a sample containing microorganisms according to the present invention, the efficiency of binding microorganisms to the solid support may increase.

Further, by using the device for separating microorganisms such as bacteria, fungi, or viruses from a biological sample according to the present invention, the microorganisms may be efficiently separated from the biological sample.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A device for separating microorganisms from a urine sample containing microorganisms, the device comprising:
   a first container comprising an H-type zeolite for pretreating a urine sample comprising microorganisms, wherein the H-type zeolite is immobilized on the first container; and
   a second container comprising a non-planar solid support to which microorganisms can bind, which is in fluid communication with the first container,
   wherein the non-planar solid support is a solid support having hydrophobicity with a water contact angle of 70 to 95° or having at least one amine-based functional group on its surface.

2. The device of claim 1, wherein the first and second containers are selected from the group consisting of a tube, a microchannel, and a microchamber.

3. The device of claim 1, wherein the second container further comprises a buffer solution storage unit.

4. The device of claim 1, wherein the non-planar solid support is a solid support having a plurality of pillars on its surface, the non-planar solid support is held within the second container and is in the form of a bead, or the non-planar-solid support has a sieve structure with a plurality of pores on its surface.

5. The device of claim 4, wherein the pillars have an aspect ratio of 1:1 to 20:1,
wherein the aspect ratio is a height of the pillar to a length of a cross section of the pillar.

6. The device of claim 4, wherein the ratio of the height of the pillars to the distance between the pillars is 1:1 to 25:1.

7. The device of claim 4, wherein the distance between the pillars is 5 to 100 μm.

8. The device of claim 1, wherein the hydrophobicity is provided by a surface of the non-planar solid support coated with octadecyldimethyl (3-trimethoxysilyl propyl)ammonium (OTC) or tridecafluorotetrahydrooctyltrimethoxysilane (DFS).

9. The device of claim 1, wherein the surface having the at least one amine-based functional group is prepared by coating the surface with polyethyleneiminetrimethoxysilane (PEIM).

* * * * *